United States Patent [19]

Hibino et al.

[11] Patent Number: 4,937,120
[45] Date of Patent: Jun. 26, 1990

[54] OPTICAL RECORDING MEDIUM AND PROCESS FOR PRODUCING THE SAME

[75] Inventors: Junichi Hibino, Kyoto; Eiji Ando, Katano, both of Japan

[73] Assignee: Director-General of the Agency of Industrial Science and Technology, Tokyo, Japan

[21] Appl. No.: 343,509

[22] Filed: Apr. 27, 1989

Related U.S. Application Data

[62] Division of Ser. No. 174,406, Mar. 28, 1988, Pat. No. 4,845,240.

[30] Foreign Application Priority Data

May 6, 1987 [JP] Japan ............................... 62-108978
Jul. 23, 1987 [JP] Japan ............................... 62-182138
Dec. 7, 1987 [JP] Japan ............................... 62-307456

[51] Int. Cl.⁵ ............................................. B32B 3/02
[52] U.S. Cl. ............................................. 428/64; 428/65; 428/913; 549/252; 369/288; 430/945

[58] Field of Search ................. 549/252; 369/288; 430/945; 346/76 L, 135.1; 428/64, 65, 913

[56] References Cited

U.S. PATENT DOCUMENTS

| | | | |
|---|---|---|---|
| 4,186,002 | 1/1980 | Heller et al. | 430/1 |
| 4,803,287 | 2/1989 | Hibino et al. | 430/343 |
| 4,895,240 | 7/1989 | Hibino et al. | 430/945 |

Primary Examiner—Patrick Ryan
Attorney, Agent, or Firm—Stevens, Davis, Miller & Mosher

[57] ABSTRACT

A long-chain keto group is introduced into the molecule of furylfulgide having no hydrophobic group to procure a good balance of hydrophilicity and hydrophobicity, thereby making it possible to obtain a uniform ultrathin film optical recording medium having photochromism of fulgide according to spin coating method or Langmuir-Blodgett method.

15 Claims, 2 Drawing Sheets

OPTICAL RECORDING MEDIUM AND PROCESS FOR PRODUCING THE SAME

This is a division of application Ser. No. 174,406, filed March 28, 1988 U.S. Pat. No. 4,845,240.

BACKGROUND OF THE INVENTION

This invention relates to an optical recording medium for making optical read and write of information by using an organic dye.

Photochromic materials are attracting attention for their availability for the erasable optical recording media owing to their specific property that they undergo a reversible change of color upon exposure to two types of light source differing in wavelength. Fulgides are known as a typical example of such photochromic materials. Fulgides are the compounds having an alkylidene group bonded to each of the two methylenic carbons of succinic anhydride or a derivative thereof, and represented by the following general formula (1):

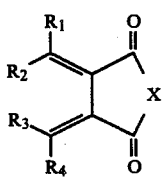

(1)

(wherein at least one of $R_2$ and $R_3$ represents an aromatic ring, and X represents O or N—R).

A large number of fulgide compounds have been known to date. Among them, fulgide (2) is one of the fulgides having the most execellent photochromic properties (JCS Perkin Trans., Part I, 202 (1981). This fulgide (2), when irradiated with ultraviolet light of 337 nm, is ring closed and converted into the red benzofuran form (3), but when the latter is irradiated with visible light of 473 nm, it returns to fulgide (2).

SUMMARY OF THE INVENTION

The present invention has for its object to provide a uniform ultra-thin film optical recording medium by realizing a good balance of hydrophilicity and hydrophobicity by introducing a long chain into the molecule of furylfulgide which has no hydrophobic group in its molecule. For attaining this object, the present invention provides a process for producing an amphiphatic photochromic compound which comprises condensing a fulgide (2) having the formula:

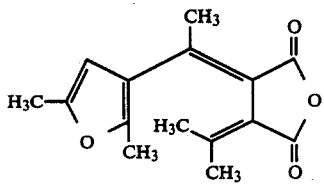

and a long-chain acid chloride having the formula:

RCOCl (where R represents an alkyl group having 5 to 31 carbon atoms) by subjecting them to a Friedel-Crafts reaction. The invention has made it possible to attain the desired reduction of film thickness by a simple operation without the least impairing the photochromism of fulgide. It is especially remarkable that the production of ultra-thin fulgide films by use of the Langmuir-Blodgett techniques was made possbile.

BRIEF DESCRIPTION OF THE DRAWINGS

In FIG. 1, curve A shows the ultraviolet visible absorption spectrum of a chloroform solution of FlF-0 and curve B shows the utraviolet visible absorption spectrum of the chloroform solution of FlF-0 which has been irradiated

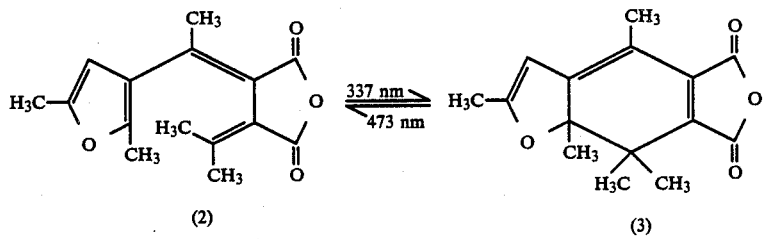

In utilization of photochromic compounds for optical recording media, light quantum detector elements, etc., it is required to reduce the film thickness in correspondence to the miniaturization in size of electronic parts. For forming a uniform ultra-thin Langmuir-Blodgett film of an organic compound, it is necessary that a hydrophobic group (for example, hydrocarbon chain) and a hydrophilic group (for example, carbonyl group) be contained in the molecule of said compound. However, since the conventional fulgide (2) has no hydrophobic group in the molecule, it has been impossible to obtain a fulgide film of a desired small thickness by the Langmuir-Blodgett technique. Also, no successful attempt of direct introduction of a hydrophobic group into the molecule of fulgide (2) has yet been reported.

with ultraviolet light and colored in yellow.

Figure 2:
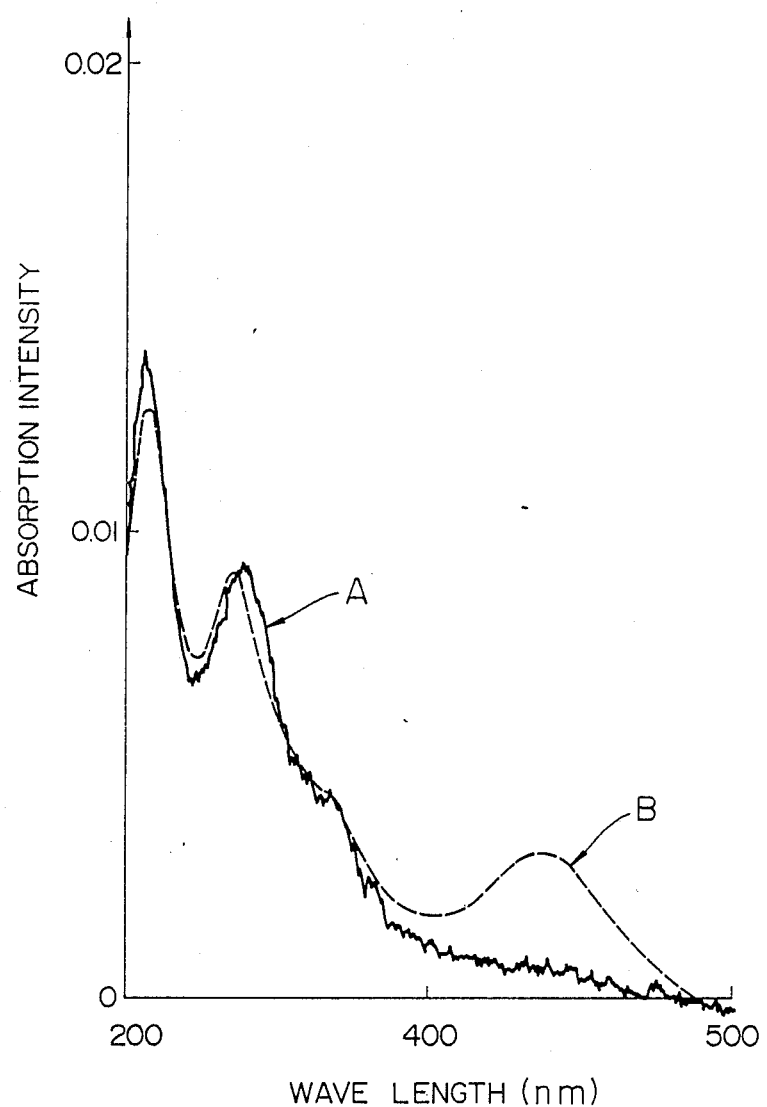

FIG. 2 shows the ultraviolet visible absorption spectra on a Langmuir-Blodgett film of the fulgide (FlF-0) used in the Examples of this invention and its colored form. Curve A shows the absorption spectrum before ultraviolet-light irradiation and curve B shows the absorption spectrum after ultraviolet-light irradiation.

DETAILED DESCRIPTION OF THE INVENTION

The invention will hereinafter be described more in detail with reference to the examples thereof.

EXAMPLE 1

The fulgide used in this example (hereinafter referred to as F1F-0) has the following chemical structure:

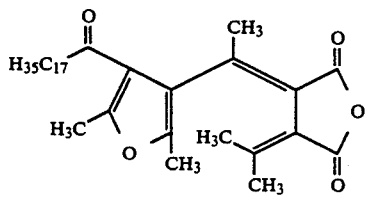

A process for synthesizing F1F-0 is described below.

Step 1

To a benzene solution containing 1 mol of 2,5-dimethylfuran and 1.5 mol of acetic anhydride, another benzene solution containing 1 mol of anhydrous tin (IV) chloride was added at 0° C. over a period of one hour. The mixed solution was stirred for several hours and then poured into ice (1.5 kg) and 5M hydrochloric acid (500 ml). The aqueous layer was extracted with ethyl acetate and the organic layer of the joined extract was washed with water and concentrated by evaporating away the solvent. The resulting product was recrystallized from ethanol to obtain 0.8 mol of ketofuran.

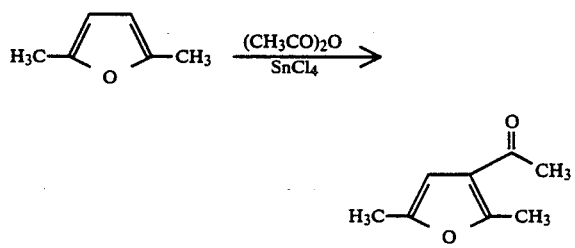

Step 2

Petroleum ether was added to 1 mol of sodium hydride, and the mixture was stirred for 5 minutes. Then the mixture was allowed to stand as it was, and after removing the supernatant, a mixture of 1.5 mol of acetone and 1 mol of diethyl succinate was added to the solution. The reaction started upon addition of one drop of ethanol to the mixture, and hydrogen was generated vigorously. After generation of hydrogen ceased, diethyl ether was added and the reaction mixture was further stirred. One hour thereafter, the reaction mixture was diluted with ethyl acetate and extracted with a 1M sodium carbonate solution. When the extract was acidified cautiously, the organic layer was separated out. This organic layer was extracted with ethyl acetate and dried over anhydrous magnesium sulfate, and then the solvent was distilled off to obtain 0.8 mol of half ester.

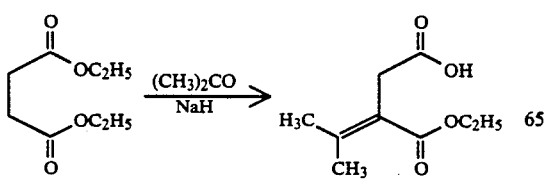

Step 3

0.8 mol of half ester obtained in step 2 was dissolved in 500 ml of ethanol, and after adding 50 ml of concentrated sulfuric acid, the mixture was refluxed under heating. Three hours thereafter, the mixture was concentrated by evaporating the solvent and the residue was diluted with ether, washed with a sodium hydrogencarbonate solution, again dried and concentrated. The resulting residue was purified by column chromatography to obtain 0.8 mol of diester.

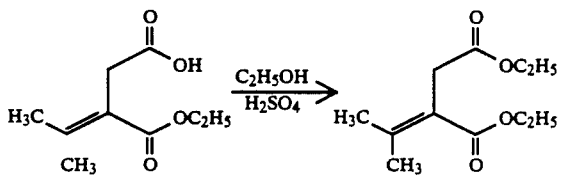

Step 4

Petroleum ether was added to 1.2 mol of sodium hydride and stirred for 5 minutes. The mixture was left as it was and the supernatant was removed. To the residue was added a mixture of 0.8 mol of ketofuran obtained in step 1 and 0.8 mol of diester obtained in Step 3, said mixture having dissolved in as small an amount of petroleum ether as possible. Addition of one drop of ethanol to the mixture initiated the reaction, and hydrogen was generated vigorously. After generation of hydrogen ceased, diethyl ether was added to the reaction mixture, followed by further stirring. One hour thereafter, the reaction mixture was diluted with ethyl acetate and extracted with a 1M sodium carbonate solution. When the extract was acidified cautiously, the organic layer was separated out. This organic layer was extracted with ethyl acetate, dried over anhydrous magnesium sulfate and concentrated by evaporating the solvent. The resulting residue was purified by column chromatography to obtain 0.5 mol of half ester.

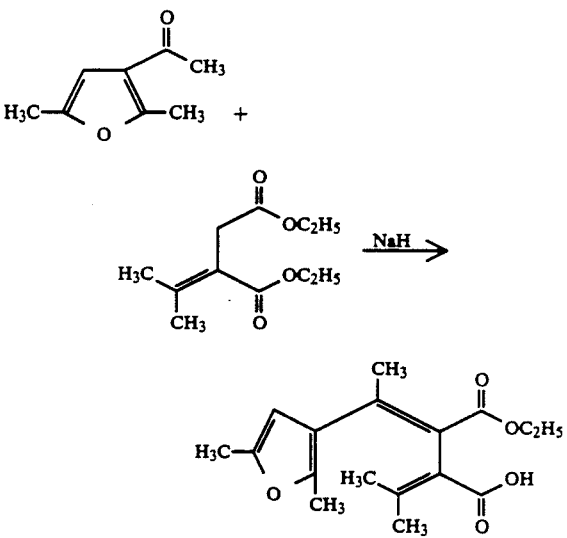

Step 5

Thus obtained 0.5 mol of half ester was dissolved in a 5% alcoholic potassium hydroxide solution and refluxed under heating for 15 hours. The resulting solution was poured into 6N hydrochloric acid and extracted with ethyl acetate. The extract was dried over anhydrous sodium sulfate and the solvent was distilled off to obtain 0.3 mol of a dicarboxylic acid. To this 0.3 mol of dicarboxylic acid was added 100 ml of acetyl chloride, and the mixture was stirred at room temperature for 10 minutes. The reaction mixture was concentrated and the residue was purified by silica gel column chromatography. The thus obtained acid anhydride was a mixture of E-form and Z-form. This mixture was separated by recrystallization to obtain 0.05 mol of an E-form acid anhydride showing photochromism.

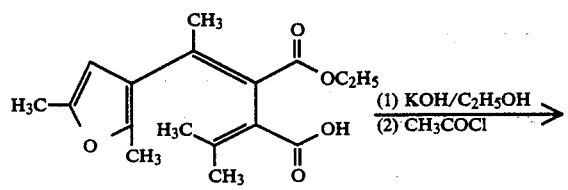

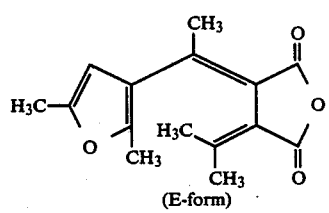
(E-form)

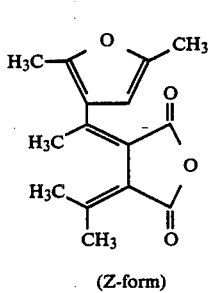
(Z-form)

Step 6

To a benzene solution of 0.05 mol of said E-form acid anhydride and 0.05 mol of stearoyl chloride was added another benzene solution of 0.1 mol of tin chloride, followed by one-hour stirring at room temperature, and the reaction mixture was poured into ice (0.5 kg) and 5M hydrochloric acid (100 ml). The aqueous layer was extracted with ethyl acetate, and the organic layer of the joined extract was washed with water, concentrated by evaporating the solvent, purified by column chromatography and further recrystallized twice from ethanol to obtain 0.01 mol of the objective fulgide FIF-0.

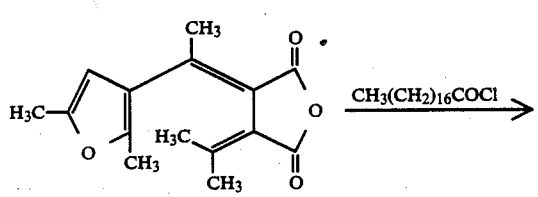

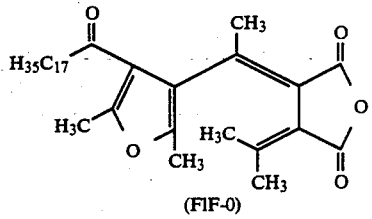
(FIF-0)

Figure 1:
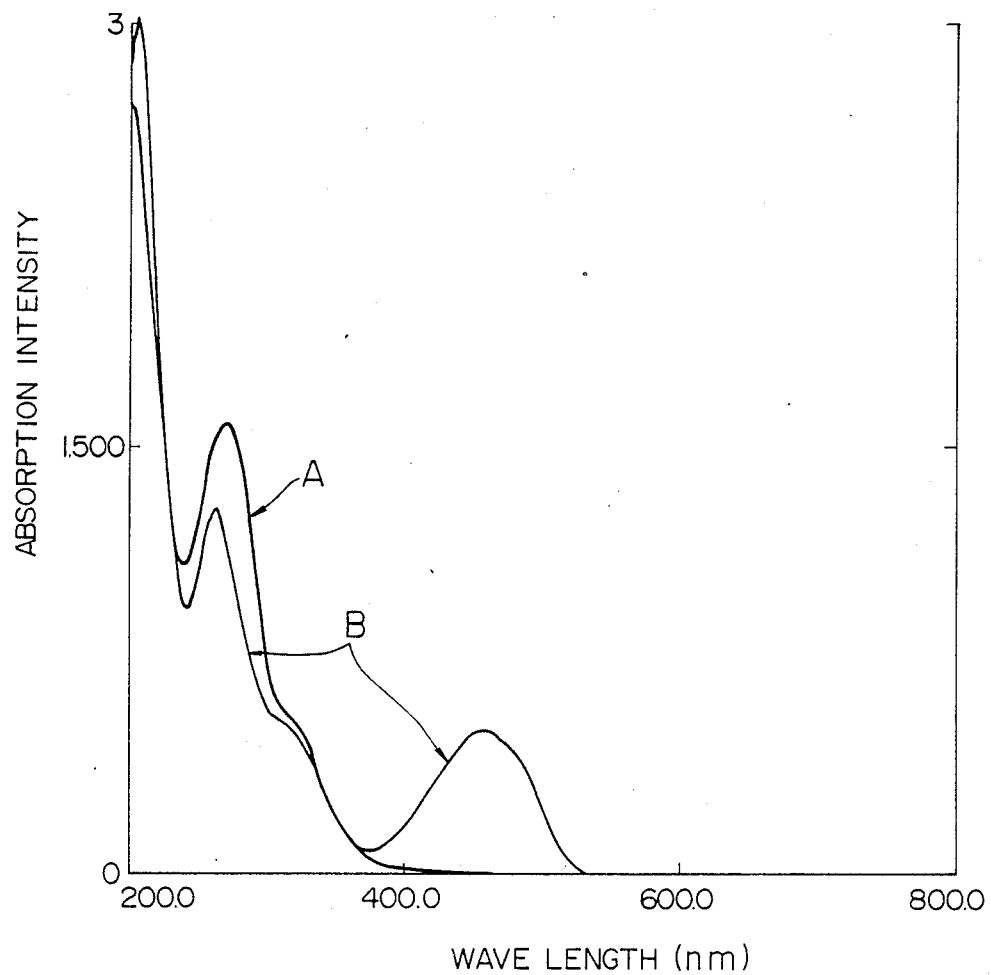
FIG. 1 shows the ultraviolet visible absorption spectra in chloroform of the fulgide (FlF-0) used in the Examples of this invention and its colored form.

The ultraviolet visible absorption spectrum of a chloroform solution of fulgide FIF-0 synthesized by the process described above is shown by curve A in FIG. 1. When this solution was irradiated with ultraviolet light of 280 nm (λ), there occurred ring closure of the fulgide and the solution was colored in yellow. The ultraviolet visible absorption spectrum of this solution is shown by curve B in FIG. 1. When this solution was further irradiated with visible light of λ=500 nm, ring opening of the fulgide took place and the solution again became chlorless. The solution, either colorless or colored, was very stable in the dark place.

EXAMPLE 2

A 0.3 mol toluene solution of FIF-0 was spin coated on silica glass (which had been cleaned with trichloroethane) at 600 r.p.m. for 60 seconds to form a recording layer. This recording layer was initially colorless, but when it was irradiated with ultraviolet light (λmax=366 nm), a reaction took place rapidly in the recording layer to cause a change into colored FIF-0, letting the recording layer assume a red color (λmax=480 nm). Further irradiation thereof with visible light (80 max=480 nm), however, caused quick restoration of the original form of FIF-0 in the recording layer to make it transparent.

EXAMPLE 3

By using a benzene solution of FIF-0, a recording layer was formed on a substrate according to the Langmuir-Blodgett method under the following conditions:
Substrate: silica glass immersed in a 10% toluene solution of chlorotrimethylsilane for 10 minutes and then washed with trichloroethane
Trough: 140 mm×600 mm
Subphase: pH 7.0 phosphate buffer; temp. 18° C.
Compression rate: 20 mm/min
Surface pressure: 18 mN/m
Number of deposition layers: 1

In this recording layer, there occured the same reversible reactions as in the recording layer of Example 1 upon irradiation with two types of light sources differing in wavelength. The thickness of this recording layer was 25 A and uniform.

Use of the benzene solution of FIF-0 of this example having a long-chain keto group having 18 carbon atoms is most desirable for forming the recording medium of this invention. Similar effect is also obtained when the carbon number (C) in the alkyl chain is from 14 to 22. In case C=greater than 31, it was difficult to obtain the starting fulgide. In case C=less than 5, it was impossible to obtain a Langmuir-Blodgett film.

EXAMPLE 4

A benzene solution of a 1:3 mixture of FIF-0 and octadecane was prepared, and a recording layer was formed by using this solution according to the process of Example 2. This recording layer was a uniform ultra-thin film like the recording layer obtained in Example 2, and in this recording layer, too, there took place the same reversible reactions as in the recording layer of Example 2 upon exposure to two types of light source differing in wavelength. Further, in the case of this example, the half-life period of F1F-0 was one week and that of the colored version was more than one day in the dark place at room temperature, which signifies a remarkable improvement of stability in comparison with single use of F1F-0 in Example 2 (the half-life period in this case being about one hour). The F1F-0 to octadecane mixing ratio of 1:2 is most preferred, but a similar effect is obtainable when said mixing ratio is in the range of 1:0.5 to 1:10.

Use of the fulgide having a $C_{18}$ long-chain keto group of this example is most desirable for producing the recording media of this invention. A similar effect can be obtained when C=14 to 22. In case C=greater than 31, it was difficult to obtain the starting fulgide. When C=less than 5, it was impossible to obtain a Langmuir-Blodgett film.

EXAMPLE 5

A benzene solution of a 1:1 mixture of F1F-0 and stearic acid was prepared, and a recording layer was formed by using this solution according to the process of Example 2. This recording layer, like that of Example 2, was a uniform ultra-thin film, and there took place the same reversible reactions as in the recording layer of Example 2 upon exposure to two type of light source differing in wavelength. Further, in the case of this example, the half-life period of F1F-0 was one week and that of the colored version thereof was more than one day in the dark place at room temperature, indicating a remarkable improvement of stability over the case where F1F-0 alone was used as in Example 2 (the half-life period in this case being about one hour). The F1F-0 to stearic acid mixing ratio of 1:1 is most preferred, but a similar effect is obtainable when said mixing ratio is in the range of 1:1.5 to 1:10.

Use of the fulgide having a $C_{18}$ long-chain keto group of this example is most desirable for producing the recording medium of this invention, but a similar effect can be obtained when C=14 to 22. In case C=greater than 31, it was difficult to obtain the starting fulgide, and when C=less than 5, it was impossible to obtain a Langmuir-Blodgett film.

What is claimed is:

1. An optical recording medium comprising a photochromic material represented by the following general formula:

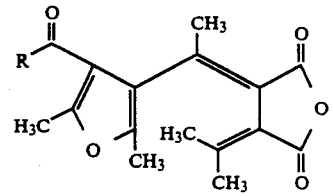

wherein R represents an alkyl chain having 5 to 31 carbon atoms.

2. An optical recording medium according to claim 1 wherein R represents an alkyl chain having 13 to 23 carbon atoms.

3. An optical recording medium according to claim 1 wherein R represents an alkyl chain having 17 carbon atoms.

4. An optical recording medium according to claim 2, having a recording layer comprising a spin coating film of a photochromic compound.

5. An optical recording medium according to claim 2, having a recording layer comprising a Langmuir-Blodgett film of a photochromic compound.

6. An optical recording medium according to claim 2, having a recording layer comprising a Langmuir-Blodgett film of a mixture of a photochromic compound and a hydrocarbon.

7. An optical recording medium according to claim 2, having a recording layer comprising a Langmuir-Blodgett film of a mixture a photochromic compound and a fatty acid.

8. An optical recording medium according to claim 3, having a recording layer comprising a spin coating film of a photochromic compound.

9. An optical recording medium according to claim 3, having a recording layer comprising a Langmuir-Blodgett film of a photochromic compound.

10. An optical recording medium according to claim 3, having a recording layer comprising a Langmuir-Blodgett film of a mixture a photochromic compound and a hydrocarbon.

11. An optical recording medium according to claim 3, having a recording layer comprising a Langmuir-Blodgett film of a mixture a photochromic compound and a fatty acid.

12. An optical recording medium according to claim 4, having a recording layer comprising a spin coating film of a photochromic compound.

13. An optical recording medium according to claim 4, having a recording layer comprising a Langmuir-Blodget film of a photochromic compound.

14. An optical recording medium according to claim 4, having a recording layer comprising a Langmuir-Blodgett film of a mixture of a photochromic compound and a hydrocarbon.

15. An optical recording medium according to claim 4, having a recording layer comprising a Langmuir-Blodgett film of a mixture of a photochromic compound and a fatty acid.

* * * * *